United States Patent [19]
Chandraratna et al.

[11] Patent Number: 5,598,845
[45] Date of Patent: Feb. 4, 1997

[54] ULTRASOUND TRANSDUCER DEVICE FOR CONTINUOUS IMAGING OF THE HEART AND OTHER BODY PARTS

[75] Inventors: P. Anthony Chandraratna, Rancho Palos Verdes; Roger A. Stern, Cupertino, both of Calif.

[73] Assignee: Stellartech Research Corporation, Mountain View, Calif.; a part interest

[21] Appl. No.: 558,503

[22] Filed: Nov. 16, 1995

[51] Int. Cl.[6] ........................................................ A61B 8/00
[52] U.S. Cl. ............................................................ 128/662.03
[58] Field of Search .............................. 128/662.03, 639, 128/640, 660.01, 660.09, 660.1

[56] References Cited

U.S. PATENT DOCUMENTS 4,947,853   8/1990   Hon ..................................... 128/662.03
5,070,880  12/1991   Gomez et al. ....................... 128/662.03

Primary Examiner—George Manuel
Attorney, Agent, or Firm—Carr, DeFilippo & Ferrell LLP

[57] ABSTRACT

An ultrasound transducer device is disclosed which is intended to be used for continuous imaging of a patient's heart or other body organs for diagnosis or monitoring. The device consists of a spherical transducer assembly held by a patch which is coated with adhesive for attaching to the body surface of a patient. Provision is made for the manual adjustment of the orientation of the transducer assembly while in place on a patient to adjust the area scanned by the transducer. An alternate embodiment of the device discloses provision for remote controlled adjustment of the transducer assembly orientation.

30 Claims, 2 Drawing Sheets

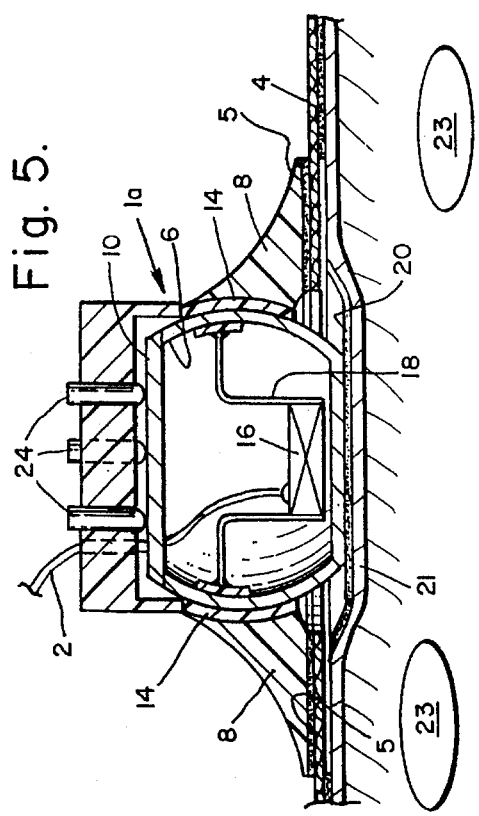
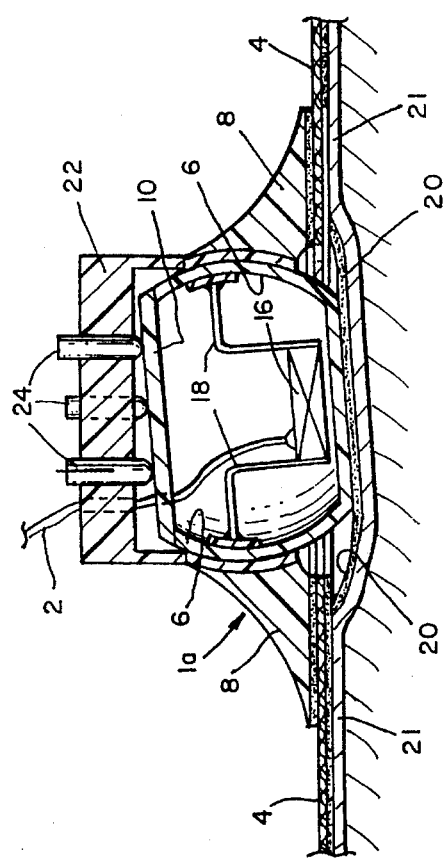
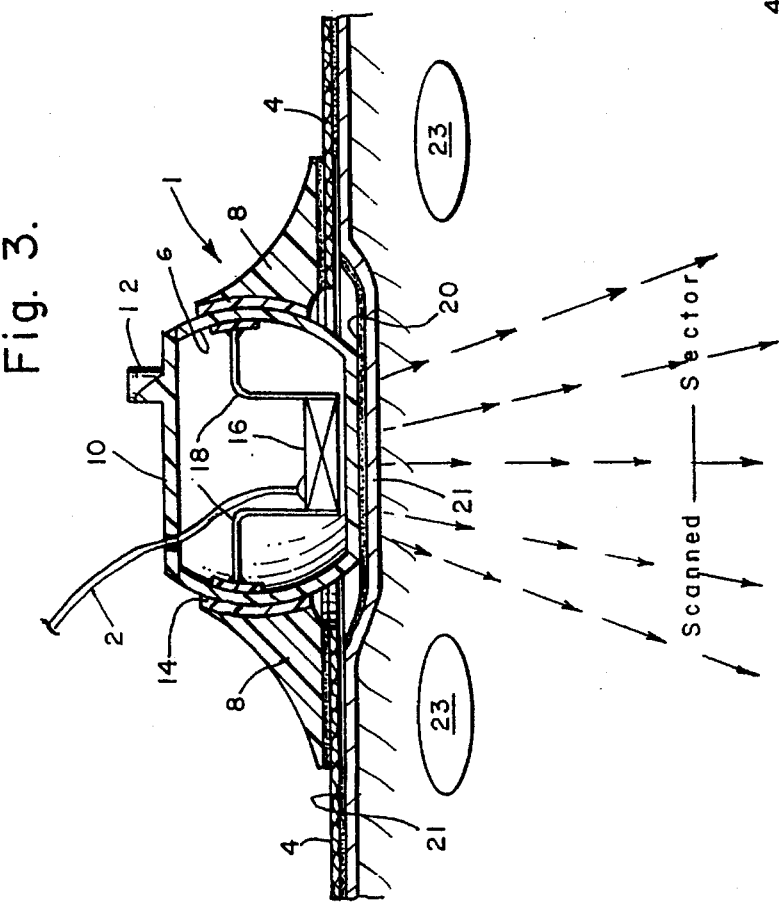

ULTRASOUND TRANSDUCER DEVICE FOR CONTINUOUS IMAGING OF THE HEART AND OTHER BODY PARTS

BACKGROUND OF THE INVENTION

1. Field of the Invention

This invention relates to devices incorporating ultrasound transducers, and more particularly to an ultrasound transducer device for the continuous imaging of body organs.

2. Background

Ultrasound technology is widely used for imaging various organs in the body and for diagnosis of tissue pathology. A variety of ultrasound transducer devices is currently available for imaging specific areas of the body. These transducer devices vary in size, shape and operating frequency depending on the age, body size of the patient and the organ that has to be imaged.

Most ultrasound examinations are performed by placing a transducer on the body surface of the patient. However, transducers may also be placed in body cavities such as the rectum and the vagina to image various abnormalities in these structures. More recently, transesophageal echocardiography has been performed by mounting a transducer at the tip of a gastroscope and introducing it into the esophagus. Transesophageal echocardiography can be used for prolonged monitoring of heart function, e.g. during open heart surgery. However, the inconvenience of swallowing the probe, the potential for complications as well as the expense, limit its use.

Commonly, in the experience of the inventors, ultrasound examinations are performed mostly by placing a probe containing an ultrasound transducer on the surface of the patient's body. This is done to make a specific diagnosis and not for prolonged monitoring of patients. An explanation for this is that the probes usually must be held by someone against the patient's body. Also, the narrow and long shape of the transducer probe precludes proper motion-free positioning for long term use. Furthermore, patient motion is restricted by the transducer probe, i.e., the patient will not be able to turn to his left when a long transducer probe is placed below the left nipple. Clancy et al in U.S. Pat. No. 5,022,410, describe an ultrasound transducer device which holds the transducer in a fixed position relative to the patient's body. They describe a device with a flexible and elongate arm which has a mount for a transducer and a means for locking the arm in a fixed position. This device however is not ideally suited for cardiac imaging, because the transducer end of the device is not designed to fit snugly into an intercostal (between ribs) space, and because even slight movements of the transducer will result in loss of or inadequate imaging for diagnostic use. Further, there is no apparent means of correcting the position of the transducer once the arm is locked in position.

A review of currently available transducer probes and the pertinent patent literature shows that none of the devices are conducive to fixation of the probe on the chest wall, and for patient comfort, for monitoring over prolonged periods of time.

In the experience of the applicants in the field of cardiology, there are several desirable potential applications for continuous imaging of the heart chambers and left ventricular function in a manner beneficial to the patients. These include:

a) Intraoperative Monitoring: Monitoring of left ventricular function during non-cardiac surgery in patients with known coronary artery disease, has long been advocated to detect and treat early myocardial ischemia. This treatment could prevent the development of serious complications such as myocardial infarction and possible death. The current method of monitoring such patients is by transesophageal echocardiography. Monitoring of left ventricular function with a transducer attached to the surface of the chest would be much more convenient, less expensive and would be routinely used.

b) Stress Echocardiography: Stress eehocardiography practice involves ultrasonic monitoring of left ventricular wall motion during exercise, using a hand held transducer probe. The appearance of a wall motion abnormality indicates the presence of myocardial ischemia. Ultrasonic images obtained during exercise are often suboptimal because of excessive motion of the transducer. A transducer attached to the chest wall would greatly improve the quality of the images obtained and improve the sensitivity of this technique for detection of myocardial ischemia.

c) In the Coronary Care Unit: Left ventricular function is a major determinant of morbidity and mortality in patients susceptible to heart attack. Continuous monitoring of left ventricular function in a coronary care unit is greatly desirable for timely preventive action, but is not currently available. An ultrasound device attached to the chest wall of the patient would facilitate continuous monitoring of left ventricular function and improve therapeutic decisions. For instance, if a large area of the patient's left ventricle stops moving during an episode of chest pain, this implies a severe proximal stenosis of a major coronary artery. Urgent cardiac catheterization and angioplasty or bypass surgery is indicated to prevent permanent damage to the heart leading to heart failure and death.

Continuous recording of left ventricular ejection fraction is also feasible using an ultrasound transducer.

d) Cardiac Catheterization: Continuous monitoring of the heart walls and heart valves with an ultrasound transducer probe attached to a patient's chest wall may facilitate the conduct and monitoring of invasive procedures. For example, during catheter balloon commissurotomy for mitral stenosis, proper positioning of the balloon across the mitral valve may be achieved by ultrasonic imaging.

e) Imaging the Inferior Vena Cava: Continuously imaging the inferior vena cava from a subcostal position may help to assess hypovolemia resulting from hemorrhage. Collapse of the inferior yens cava indicates a severe hemorrhage. Return of the inferior vena cava to normal dimensions would indicate adequate volume replacement.

Besides cardiac imaging, there are other areas of body diagnosis which would benefit from the use of an ultrasound transducer being attached to the body surface. For example, a transducer device could be placed on the abdomen to monitor laparoscopy.

In view of the foregoing potential applications, it would be a significant medical diagnosis and monitoring advance over presently available techniques, to provide an ultrasound transducer device for continuous imaging of the heart and other body organs.

SUMMARY OF THE INVENTION

The invention is an ultrasound transducer mounted inside a semi-spherical enclosure having a bottom surface conforming to the chest wall, moveably mounted and held in place by an adhesive patch to be secured to the skin surface. Provision is made for the transducer enclosure to be manually rotated or tilted through an angle to adjust the scanning area. In an alternate embodiment, provision is made for the transducer scanning angle to be remotely adjusted utilizing vertical pins that bear on the top surface of the transducer enclosure.

It is therefore a principal object of this invention to provide an ultrasound transducer device, which when secured to the skin, will enable continuous imaging of the heart and other body structures for monitoring or diagnosis purposes. Another object of the present invention is to provide an ultrasound transducer which can be manually or remotely moved through an angle, so that the ultrasonic beam can be optimally directed to obtain accurate imaging of the heart or other body structure. An advantage of this invention over presently available transesophageal transducer probes is its lower cost.

Further objects and advantages of the invention will be apparent from studying the following portion of the specification, the claims and the attached drawings.

BRIEF DESCRIPTION OF THE DRAWINGS

FIG. 3 is a partial cross-section view of the present invention device taken along line 3—3 of FIG. 2, particularly showing the device adhered to a patient's chest and in place for projecting an ultrasound scanning beam;

FIG. 5 is a partial cross-section view of the alternate configuration device taken along line 5—5 of FIG. 4, showing the device adhered to a patient's chest; and FIG. 6 is a partial cross-section view of the alternate configuration device taken along line 5—5 of FIG. 4, showing the device adhered to a patient's chest, and useful in explaining the action of top actuating pins in tilting the ultrasound transducer to adjust the angle of the ultrasound beam.

DESCRIPTION OF THE PREFERRED AND ALTERNATE EMBODIMENTS

Figure 1:
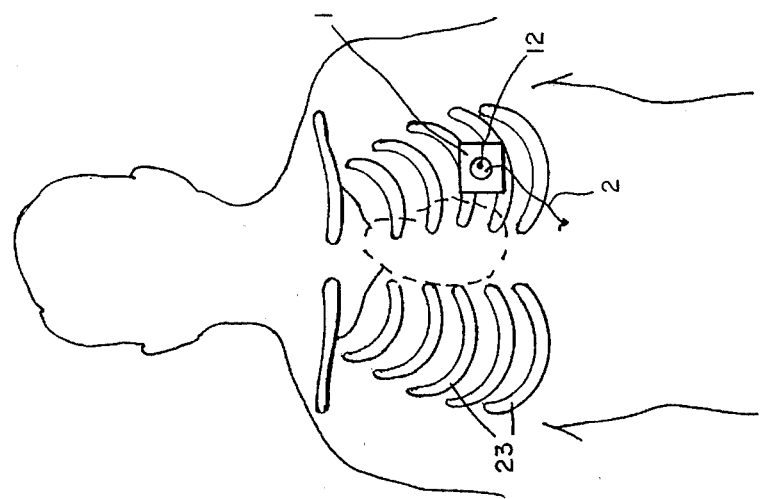
FIG. 1 is a view showing the present invention ultrasound transducer device affixed on a patient's chest, particularly on his left side between the ribs for monitoring the heart.

Referring particularly to the drawings, there is shown in FIG. 1 a view of a low profile ultrasound transducer device 1 according to the present invention, positioned adhered to the chest wall in an intercostal space (between the ribs 23). A conductor signal means 2 is shown coming out of the top 10 of the transducer enclosure. This conductor signal means 2 is used to transmit ultrasound activating signals to the transducer, producing a scanning beam into the patient's tissues, and to transmit back to receiving display monitors the ultrasound signals reflected from the body parts being scanned. The conductor signal means 2 may be co-axial cable or a twisted pair of wires as required by the application.

Figure 2:
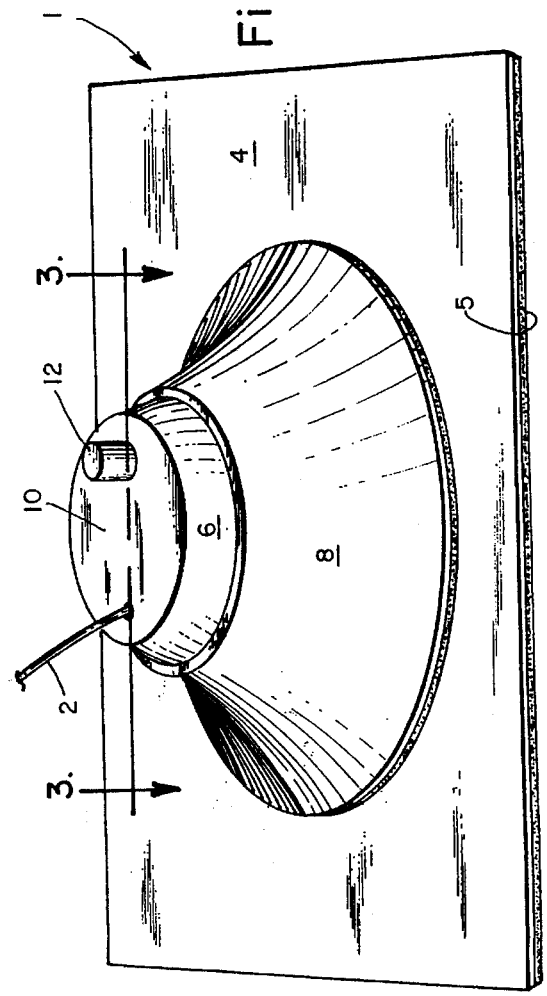
FIG. 2 is a perspective view of a preferred configuration of the present invention device, where the center portion of the device is particularly shown enlarged for clarity.

Refer now to FIGS. 2 and 3 which are respectively, a perspective view of the preferred embodiment of the device 1 and a partial, cross-section view of the device 1 mounted on a patient's chest, taken along line 3—3 of FIG. 2. It should be noted that the center portion of the device in both figures is shown in larger size in proportion to its surrounding adhesive patch 4. This is done to ensure clarity of detail in the construction of the device. The actual center portion of the device projects only a little above the surface of adhesive patch 4, and an even smaller amount ( about 0.1 inch) below it, so that the device can truly be said to be low in profile.

The device comprises a spherical transducer assembly mounted and retained in a holding pad by means permitting the transducer assembly attitude to be adjusted and rotated a small amount laterally or vertically, while maintaining a frictional grasp sufficient to hold the transducer assembly in its adjusted position.

The transducer assembly comprises a spherical shaped, hollow enclosure 6 with an open top and flat bottom, a top cover 10 which is cemented to the top of the enclosure 6, an acoustic transducer means 16 mounted inside the bottom of the enclosure 6 by a mounting structure 18 which is attached to the inside walls of the enclosure 6, and a conductor signal means 2 which is connected to the transducer means 16 and which exits the assembly through a hole in the top cover 10.

The top cover 10 includes a vertical projecting stub 12 which is to be used for manually adjusting and rotating the transducer assembly in relation to its holding pad. The enclosure 6 and top cover 10 are molded from a plastic material since this material provides the desired properties of strength, workability, light weight and low cost. The transducer mounting structure 18 inside the enclosure 6 may also be of plastic material and could be molded as part of the enclosure 6 in one piece, providing economic manufacture and assembly.

The acoustic transducer means 16 utilizes piezoelectric elements arranged in a specific manner: e.g., a phased array, an annular array, a mechanical scanned single element or a variation of arrays. These piezoelectric arrays are well known and available to industry. Operation frequencies of the device will typically be in the range of 2.0 to 10 MHz and are determined by the external equipment driving the transducer array.

A phased array is an array that steers and focuses the beam electronically with short time delays. On the other hand, an annular array produces a scanning beam with different characteristics. An annular array is made up of elements arranged in several concentric rings and operated as phased to provide electronic focal control.

The holding pad comprises a cloth portion 4 having a circular hole in its center and an adhesive layer 5 affixed to its underside, an annular axially projecting collar 8 which is attached to the top side of the cloth portion 4 around the circular hole at the cloth portion center, and a ring portion 14 which fits inside the collar 8 and is attached to it. The inner surface of the ring portion 14 is curved and sized in diameter to fit closely over the outside surface of the transducer enclosure 6.

The ring portion 14 and the collar 8 are initially split into two halves prior to assembly of the transducer assembly, which facilitates assembly of the device. Both the ring portion 14 and the collar 8 are made of plastic material, formed to the required shape. If so desired, they could be combined in one piece.

The ring portion 14 inner surface is roughened to provide a friction engagement with the outside surface of the transducer enclosure 6. This is done to ensure that the ring portion 14 will hold the transducer enclosure 6 in position without further movement, after the enclosure position has been manually adjusted for scanning the patient.

In use, the assembled device 1 is adhered to the skin surface 21 of the patient in an intercostal position between the ribs 23 if the heart is being monitored, or on another part of the body if another body organ is being monitored. An aqueous gel 20 is placed on the skin 21 surface so that the gel 20 is between the transducer assembly and the patient's body, forming a coupling medium. The gel 20 eliminates any air layer between the transducer assembly and the tissue, facilitating sound passage into and out of the tissue.

Figure 4:
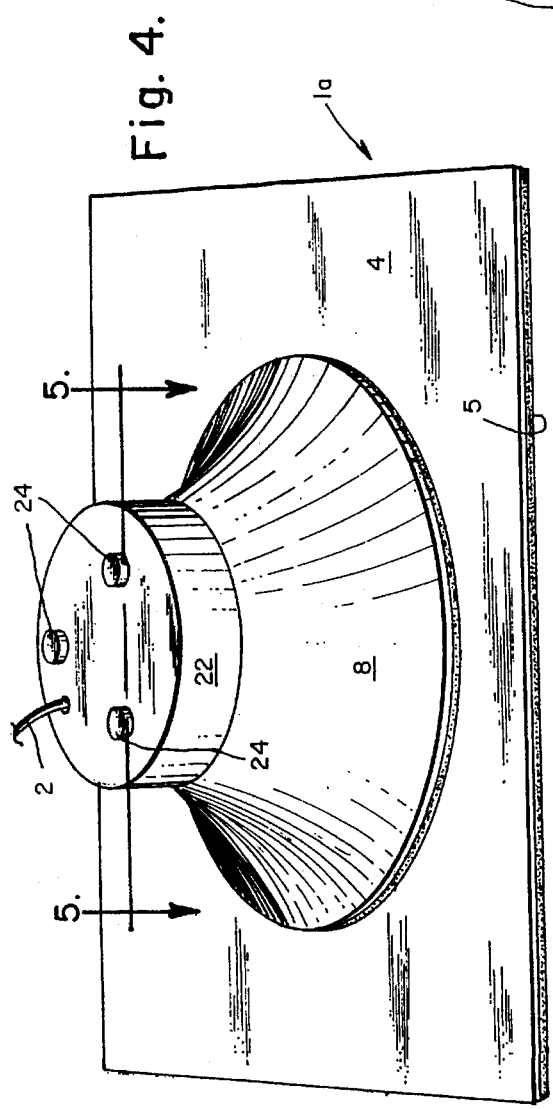
FIG. 4 is a perspective view of an alternate configuration of the present invention device, where the center portion of the device is particularly shown enlarged for clarity.

As depicted in FIGS. 2 and 3, the ultrasound transducer device is intended to be placed onto the desired position by the nurse or doctor, who applies finger pressure to the top 10 and the stub 12 of the transducer assembly and manipulates the transducer assembly rotational position to the desired orientation. The scanned images can then be transmitted to any location for monitoring. However, in certain circumstances, it may be desirable to remotely adjust the transducer assembly orientation. To meet this possible need, an alternate embodiment of the invention device, permitting remote orientation adjustment, is shown in FIG. 4.

Partial cross-sectional views of the alternate device located on a patient's chest, taken along line 5—5, are shown in FIGS. 5 and 6. The alternate embodiment of the device is identical to the preferred embodiment shown in FIGS. 2 and 3 except for the addition of an adjusting assembly to the device. All the other parts of the transducer assembly and holding pad are the same as those described earlier for the preferred embodiment and are identified in FIGS. 4, 5 and 6 with the same numerals as are used in FIGS. 2 and 3.

The adjusting assembly comprises an actuator support structure 22 and three actuating pins 24. The support structure 22 is a short cylinder portion, open at one end, having a thick closed end and short length, rigid circumferential walls. There are four axially oriented holes in the closed end of the actuator support structure 22. Three of the holes are arranged in a circle and are approximately 120 degrees apart. These three holes are sized to accommodate the actuating pins 24, which are located within the holes. The fourth hole, which is located near the periphery edge of the structure end, is sized to accommodate conductor means 2.

When the adjusting assembly is added to the remainder of the ultrasound transducer device, the conductor means 2 is pulled through the wire hole in the actuator support structure 22, and the structure wall ends are cemented to the top edge of the collar 8 or ring portion 14 of the holding pad as shown in FIGS. 5 and 6, holding the adjusting assembly rigidly in place above the transducer assembly. In this manner, the three actuating pins 24 will all bear on the top cover 10 of the transducer assembly.

FIG. 6 shows the result of an operator pushing down on one or two of the actuating pins 24. This action causes the enclosure 6 to swivel with one side downwards inside the ring portion 14, placing the face of the transducer means 16 at an angle to the patient's chest surface and thereby adjusting the area scanned by the transducer means.

It is intended that the actuator pins 24 be pushed either manually by a doctor or nurse, or by a remotely controlled mechanism. The support structure 22 top surface and edge is large enough to support such a mechanism, which could be very small in size. The mounting of an adjusting assembly to the top of the ultrasound transducer device is thus seen as facilitating remote adjustment of the device scanning area.

It is sincerely believed that the ultrasound transducer device described herein, being suitable for continuous imaging of the heart and other organs, will particularly be welcomed by cardiologists and nurses working in the coronary care unit (CCU) of any hospital. The use of this device will provide valuable continuous information about heart function in patients who have complications related to myocardial infarction (MI) and in response to treatment. Its use can be instrumental in alerting the physician or nurse to the need for emergency treatment to avoid patient death.

From the above description, it is clear that both the preferred and alternate embodiments of the device achieve the objects of the present invention. Alternative embodiments and various modifications may be apparent to those skilled in the art. These alternatives and modifications are considered to be within the spirit and scope of the present invention.

Having described the invention, what is claimed is:

1. An ultrasound transducer device for attachment to a surface of the body of a patient, and for providing continuous imaging of organs inside said body surface, said transducer device comprising:

(a) a transducer assembly including
   a transducer enclosure;
   supporting means for mounting an ultrasound transducer means inside said enclosure;
   ultrasound transducer means mounted on said supporting means for transmitting and receiving ultrasound beams from which to create scan lines forming an image of a surface on an organ inside said body surface; and
   conductor means for providing electrical signal connections between said transducer means and externally located transducer scanner and display equipment;

(b) a holding pad defining an opening;

(c) means for attaching said holding pad to a surface of the body of a patient; and (d) means for movably securing said transducer enclosure to said holding pad such that said transducer enclosure protrudes through said opening, and enabling said transducer enclosure to be rotated to adjust the imaging surface scanned by said ultrasound transducer means while said transducer enclosure is in place against the body surface of a patient, and to provide continuous scanning.

2. The ultrasound transducer device recited in claim 1, wherein said transducer enclosure is shaped semi-spherically with a transmission surface protruding through said opening, and a substantially flat cover surface opposite said transmission surface, and has a low profile in the direction between said cover surface and said transmission surface.

3. The ultrasound transducer device recited in claim 2, wherein said enclosure comprises a stub portion which projects from said cover surface, facilitating manual adjustment of the orientation of said transducer enclosure relative to said pad.

4. The ultrasound transducer device according to claim 1, wherein said conductor means comprises coaxial cable.

5. The ultrasound transducer device according to claim 1, wherein said conductor means comprises a twisted pair of insulated wires.

6. The ultrasound transducer device according to claim 1, wherein said means for movably securing said transducer enclosure includes an annular axially projecting collar attached to said holding pad and having a concave inside surface over said opening and sized to fit closely around and grip the outside surface, while also permitting manual adjustment of the orientation, of said transducer enclosure.

7. An ultrasound transducer device for attachment to a surface of the body of a patient, and for providing continuous imaging of organs inside said body surface, said transducer device comprising:
(a) a transducer assembly including
a transducer enclosure;
supporting means for mounting an ultrasound transducer means inside said enclosure;
ultrasound transducer means, mounted on said supporting means for transmitting and receiving ultrasound beams from which to create scan lines forming an image of a surface on an organ inside said body surface; and
conductor means for providing electrical signal connections between said transducer means and externally located transducer scanner and display equipment;
(b) a holding pad defining an opening;
(c) means for attaching said holding pad to a surface of the body of a patient;
(d) means for rotatably securing said transducer enclosure to said holding pad; and
(e) means for remotely adjusting the orientation of said transducer enclosure relative to said holding pad;
said transducer enclosure protruding through said opening;
said means for remotely adjusting the orientation of said transducer enclosure serving to adjust the location of the imaging surface scanned by said ultrasound transducer means while said transducer enclosure is in place against the body surface of a patient and providing continuous imaging of an organ inside said body surface.

8. The ultrasound transducer device recited in claim 7, wherein said transducer enclosure is shaped semi-spherically with a transmission surface protruding through said opening, and a substantially flat cover surface opposite said transmission surface.

9. The ultrasound transducer device recited in claim 7, wherein said means for remotely adjusting includes an adjustment assembly mounted on said means for rotatably securing and adjacent said transducer enclosure opposite said pad,
said adjustment assembly including a cylindrical member and three pin members, said cylindrical member being open at its lower end and having a thick upper end cap and short, rigid circumferential walls, said upper end cap including three holes disposed approximately 120 degrees apart and sized to accommodate a pin member;
said pin members projecting against said transducer enclosure and facilitating remotely adjusting the orientation of said transducer enclosure by a person or by a mechanism pushing on one or more of said pins, thereby causing said transducer enclosure to rotate to another position and adjust said surface of an organ scanned by said ultrasound transducer means.

10. The ultrasound transducer device according to claim 7, wherein said conductor means comprises coaxial cable.

11. The ultrasound transducer device according to claim 7, wherein said conductor means comprises a twisted pair of insulated wires.

12. The ultrasound transducer device according to claim 7, wherein said means for rotatably securing said transducer enclosure includes an annular axially projecting collar attached to said holding pad and
having a concave inside surface over said opening and sized to fit closely around and grip the outside surface, while also permitting manual adjustment of the orientation, of said transducer enclosure.

13. An ultrasound transducer holder comprising:
a holding pad having
a surface attachable to a human body,
an opening through said pad, and
a socket defining a holding space disposed around said opening; and
a transducer assembly including an enclosure which houses an ultrasound transducer and is disposed in said holding space and frictionally held by said socket such that the orientation of said enclosure may be adjusted about an axis parallel to said surface;
whereby said transducer may be directed to communicate ultrasonically with a body part positioned close to said opening.

14. The holder of claim 13 further comprising adhesive disposed on said surface.

15. The holder of claim 14 wherein said adhesive comprises an adhesive patch having an area greater than that of said surface.

16. The holder of claim 14 wherein said surface is attachable to a chest wall.

17. The holder of claim 16 wherein said surface is shaped to fit against an intercostal space.

18. The holder of claim 13 wherein said transducer holder has a low profile in the direction normal to said surface.

19. The holder of claim 18 wherein said assembly further comprises a cover disposed on said enclosure.

20. The holder of claim 19 wherein said holding pad further comprises an adjusting assembly for adjusting the orientation of said enclosure with respect to said surface.

21. The holder of claim 19 wherein said adjusting assembly further comprises actuator means for acting on said enclosure.

22. The holder of claim 21 wherein said actuator means comprises a plurality of pins.

23. The holder of claim 13 wherein said surface lies substantially in a plane.

24. The holder of claim 23 wherein said enclosure can be turned around any axis parallel to said plane.

25. The holder of claim 24 wherein said enclosure can be mined around an axis perpendicular to said plane.

26. The holder of claim 25 wherein said holding space is spherical and said enclosure is semi-spherical. spherical.

27. The holder of claim 26 wherein said spherical holding space extends through said opening.

28. The holder of claim 27 wherein said opening is a circular hole.

29. The holder of claim 26 wherein said holding pad comprises a collar which forms said surface and a ring portion with a concave surface corresponding to a zone of a sphere which forms said socket.

30. The holder of claim 29 wherein said concave surface is roughened.

\* \* \* \* \*